Figure 1:
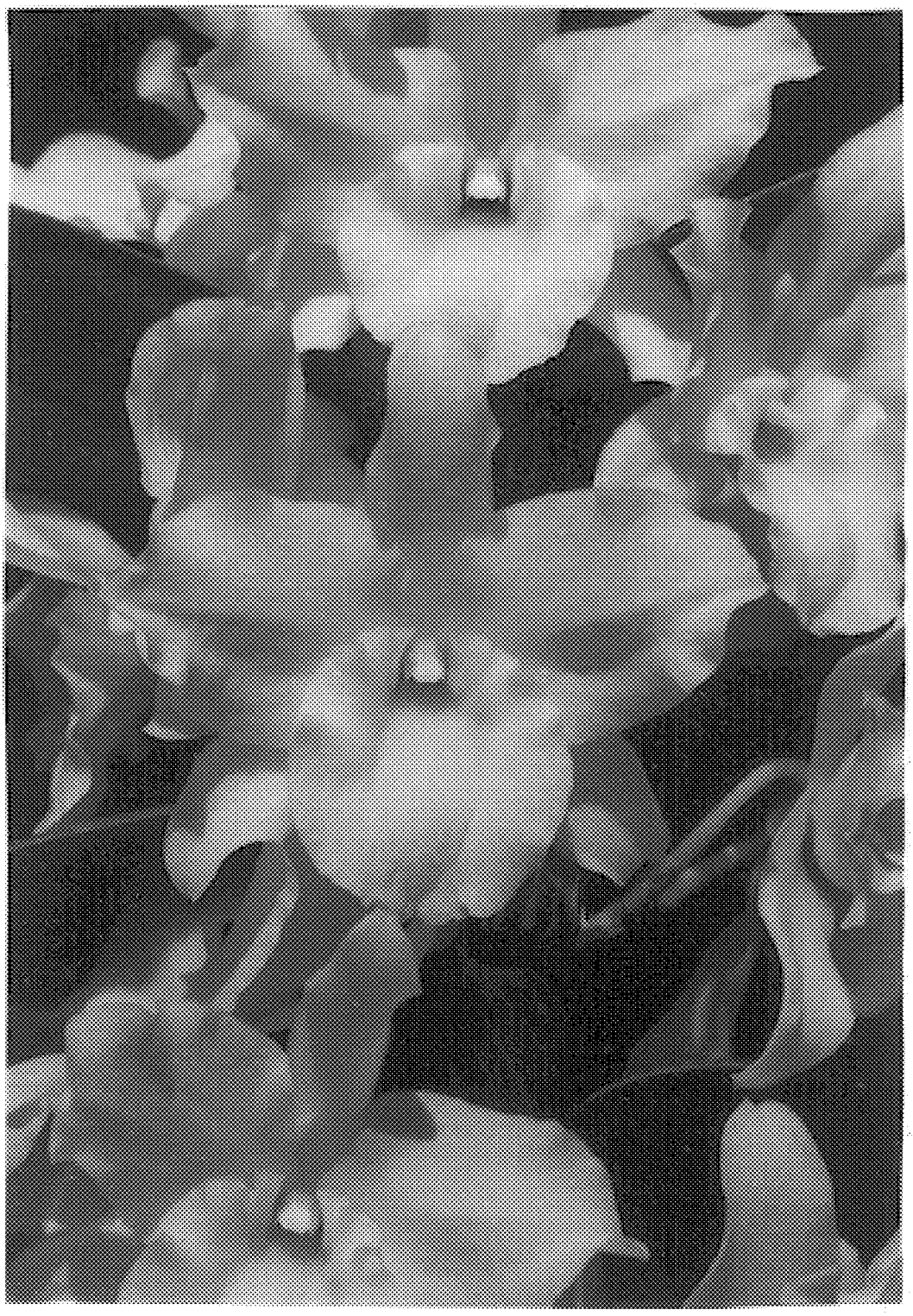

US00PP11321P

United States Patent [19]

Yamamoto

[11] Patent Number: Plant 11,321

[45] Date of Patent: Apr. 4, 2000

[54] DENDROBIUM PLANT NAMED 'SNOW KING'

[76] Inventor: Jiro Yamamoto, 1-12-30 Hamano, Okayama City, Okayama 700, Japan

[21] Appl. No.: 08/924,665

[22] Filed: Sep. 5, 1997

[51] Int. Cl.[7] ..... A01H 5/00

[52] U.S. Cl. ..... Plt./311

[58] Field of Search ..... Plt./311

[56] References Cited

PUBLICATIONS

GTITM UpovRom Citation for 'Seamary Snow King' as Per JP PBR 7024, Jul. 21, 1994.

Application for Registration of Species (Variety), No. 7024, filed Jul. 21, 1994 (S. Yamamoto, inventor)—copies in English and Japanese.

Certificate of Registration No. 6,423 for Registration Variety Sea Mary 'Snow King' under Japanese Plants Variety Regulation Article 12, Item 4, No. 1, dated May 22, 1988 (copies in English and Japanese).

Sander's List of Orchid Hybrids Addendum 1991–1995; pp. 263,286,301,315,327,329,332, and 334.

*Primary Examiner*—Howard J. Locker
*Assistant Examiner*—Kent L. Bell
*Attorney, Agent, or Firm*—Banner & Witcoff, Ltd.

[57] ABSTRACT

A new and distinct variety of orchid, more particularly a Dendrobium hybrid cultivar plant, having durable, pure white flowers is disclosed. The plant's vigorous character makes it particulaly well suited as a small or medium size potted plant.

1 Drawing Sheet

DISCOVERY OF THE NEW VARIETY

The orchid of this application was discovered by the applicant in January 1992 as an outstanding member of a large population of seedlings obtained by crossing Dendrobium Lovely Virgin 'Angel' (unpatented) with Dendrobium Cassiope 'Seto' (unpatented) The mother plant, Lovely Virgin 'Angel' is a cross between 'Fujimusume' and 'Cherry Grow' and has a light lavender large size flower with a yellow eye at the lip. It blooms well and is used as a potted plant. The father plant, Cassiope 'Seto' is a cross between *Dendrobium moniliforme* and *Dendrobium nobile* and has white flowers with a soft blurry pink color at the outside edges. The center of the flowers is white. It blooms well and has a tendency to bloom early. These two varieties were cross-bred on Jan. 23, 1989, and their 300 seedlings were cultivated.

In January 1992 the plant of the new variety was immediately recognizable as superior in its flowering and general growth habit to all other seedlings obtained from this cross. When the first flowers were observed the cane was 14 cm tall. It had seven nodes, on five of which were 12 flowers. After the new variety had been observed for a period of time its other features of vigorous and early blooming were also noted. The following year, in 1993, pods formed on the pseudobulbs, and a 23 cm cane had seven nodes. Six of the nodes had 14 flowers. In 1994, on a 36 cm cane with 12 nodes, 10 nodes had 26 flowers. Thus, the new variety blooms exceptionally well.

ASEXUAL REPRODUCTION

Since its discovery in January 1992 the variety has been grown in the applicant's greenhouse at Yamamoto Dendrobium Nursey, Hamano 1-12-30, Okayama City, Japan. During this time a number of plants of the new variety have been asexually reproduced, by the use of stem propagation, tissue culture, and by dividing the plants.

All of the propagations reproduced true to the original in both plant, flower and other characteristics, with no signs of mutation. All plants in the variety have continued to be readily distinguishable from both parents in flower quality, plant growth habit and other characteristics. The new variety has been designated as Dendrobium Sea Mary 'Snow King'.

DESCRIPTION OF THE PHOTOGRAPH

The photograph shows the colors of the new variety as nearly true as possible with an illustration of this type.

FIG. 1 is a closeup view of a spray of flowers typical of the new variety.

DESCRIPTION OF THE PLANT AND FLOWERS

The plant with its flowers is illustrated in the color photographs accompanying this specification. The chart used in the identification of the colors is that of The Royal Horticultural Society (R.H.S. Colour Chart). The age of the pseudobulb on the plant described is 1–2 years.

The new variety 'Snow King' has a number of features which suit it for use as a small or medium-sized potted plant. It has a vigorous growth rate. The cane is fairly thick and sturdy, and grows as high as 45 cm. The cane blooms especially well. On one particular cane 35 cm high with 12 nodes, 25 flowers bloomed on 10 of the nodes. The plant is an early bloomer and can be used as a forcing culture.

The dorsal sepal, lateral sepals, and petals are pure white in color, with a lip that is slightly greenish cream at the eye. Flower durability is excellent, with a lifespan longer than that of flowers of the closest comparable variety, Dendrobium Sailor Boy 'Shirasagi' (a cross between Fortune and Beautiful Egg; unpatented). The plant blooms well even on short canes; on a particular cane which was 13 cm tall, flowers bloomed on 5 out of 7 nodes. Compared with 'Shirasagi', the flowers of 'Snow King' appear to bloom more densely, because of the shorter internodes of the new variety. The following internode dimensions are typically observed: top, 3.2 cm long and 1.8 cm wide; bottom, 5.2 cm long and 1.5 cm wide. Whereas the flower buds of 'Shirasagi' appear in numbers only after the cane has reached 25–30 cm, 'Snow King' produces flower buds on canes as short as 13–15 cm. The flowers of 'Shirasagi' are white, with the lip being more of a soft cream color.

'Snow King' is a deciduous type of orchid. If grown in a greenhouse and maintained at over 17° C. at night, new pseudobulbs will appear and will be mature cane by mid-July or early August. Within the winter to spring of that same year, flower buds appear on the new pseudobulbs. The buds can be small, medium, or large. Small buds are typically 1.4 cm long and 0.5 cm wide; their color is 146C. Medium buds are typically 1.8 cm long and 0.8 cm wide; their color is 145A. Large buds are typically 3.2 cm wide; their color is 145C. All buds are oblong in shape and firm in texture.

In cooler temperatures (40°–50° F.) the plant will generally bloom for three months. In Hawaii, at temperatures between 70°–80° F., the plant will bloom for 5–6 weeks. Off the plant, refrigerated and moist, the bloom will last 7–10 days. On the plant, the bloom will last 5–6 weeks.

The stamens, style, and stigmas are fused into a single column, possessing an anther with pollen grains united into a set of two-each pollinia, which are covered by an anther cap. The stigma is located under the column behind the pollinia. The ovary is inferior, with three carpels present.

Specific features of the plant are listed below.

Size of plant: Medium.
Plant posture: Erect.
Pseudobulb:
- *Frontage.*—Narrow rectangular.
- *Cross section.*—Irregular round.
- *Height.*—35–50 cm.
- *Diameter.*—11–20 mm.
- *Color.*—146C.

Leaf:
- *General shape.*—Ellipse.
- *Shape of tip.*—Cuspidate.
- *Foliage.*—Sessile.
- *Base of foliage.*—Sheathed.
- *Vertical cross section.*—Almost flat.
- *Direction of leaf.*—Horizontal.
- *Length.*—12.1 cm.
- *Width.*—4.7 cm.
- *Surface color.*—Green, 137B.
- *Underside color.*—Light green, 146C.
- *Thickness.*—0.6–1.0 mm.
- *Variegation.*—None.
- *Color of sheath.*—145C.
- *Pubescence on leaf & sheath.*—None.
- *Number of leaves.*—11–15 on largest pseudobulb cane.

Flowers:
- *Arrangement.*—Raceme.
- *Number of blooms per stem.*—3–5.
- *Thickness of flower stem.*—1.1–2.0 mm.
- *Length of flower stem.*—11–30 mm.
- *Color of flower stem.*—157D.
- *Direction of flower stem.*—Slanting upward.
- *Size of bract leaf.*—4.6 cm long, 1.9 cm wide.
- *Color of bract leaf.*—Light green, 148B.
- *Single or double bloom.*—Single.
- *Mode of bloom.*—Flat.
- *Length of spur.*—3–5 mm.
- *Width of flower.*—61–80 mm.
- *Vertical length of flower.*—61–80 mm.
- *Dorsal sepal.*—Shape: elliptical. Tip: Cuspidate. Degree of twist: none. Degree of curl: flat. Waves at edges: none. Width: 16–20 mm. Length: 31–40 mm. Margin: entire. Base: sessile. Tip: cuspidate. Degree of twist: none. Direction of curl: flat. Waves at edges: medium undulation. Width: 16–20 mm. Length: 31–40 mm. Margin: entire. Base: sessile, with short mentum, approximately 0.7 0.8 cm.
- *Petals.*—Shape: rectangular. Tip: cuspidate. Degree of twist: none. Direction of curl: flat. Waves at edges: medium undulation. Cut at edges: medium. Direction of protrusion from stem: perpendicular. Width: 21–30 mm. Length: 31–40 mm.
- *Lip.*—Shape of the lip: obovate/elliptic. Cross section: flat. Existence of twist: none. Waves at edges: medium undulation. Cut at edges: medium. Existance of pubescence: none. Appendage at the base of the flower: none. Width: 26–30 mm. Length: 31–40 mm. Margin: entire. Base: nearly convolute, open approximately 1–2 times the width of the column.
- *Color of total flower.*—White with slight greenish cream eye.
- *Color of dorsal sepal.*—Inner side pattern: single color with a tinge of pinkish purple (75D) at the margins extending from the central portion to the tip. Inner side base color: 155C. Outer side pattern: single color with a tinge of pinkish purple (75D) at the margins extending from the central portion to the tip. Outer side base color: 155C.
- *Color of lateral sepal.*—Inner side pattern: single color. Inner side base color: 155C. Outer side pattern: single color. Outer side base color: 155C.
- *Petal.*—Inner side pattern: single color. Inner side base color: 155C. Outer side pattern: single color. Outer side base color: 155C.
- *Lip.*—Inner side pattern: dots/blurred. Inner side base color: 155C. Inner side color of Central eye: 150C. Outer side pattern: single color. Outer side base color: 155C.
- *Column.*—Outer side pattern: single color. Outer side base color: 144D.
- *Pollen color.*—155D.
- *Fragrance of flower.*—None.
- *Bloom period.*—Winter/Spring.
- *Duration of bloom.*—30 days.
- *Irregularity of flower form.*—None.
- *Dropping of lip.*—None.
- *Discoloring of lip.*—None.
- *Cold and heat durability.*—The plant can withstand temperatures above freezing and up to 104 ° F.
- *Resistance to disease.*—Average the exact durability is unknown.
- *Resistance to insects.*—average.
- *Development of offshoots.*—Minor with too much nitrogen, offshots emerge from the top of the cane instead of flowers; otherwise, offshoots emerge from the base of the plant.

I claim:

1. A new and distinct Orchid plant, as illustrated and described.

* * * * *